United States Patent [19]

van Dijken et al.

[11] Patent Number: 4,701,414

[45] Date of Patent: Oct. 20, 1987

[54] METHOD FOR PRODUCING ETHANOL FROM XYLOSE-CONTAINING SUBSTANCE

[76] Inventors: Johannes van Dijken, Geerbron 18, Pynacker; Alexander Scheffers, Sint Jorisweg 21, Delft, both of Netherlands

[21] Appl. No.: 694,458

[22] PCT Filed: Apr. 26, 1984

[86] PCT No.: PCT/SE84/00155

§ 371 Date: Dec. 31, 1984

§ 102(e) Date: Dec. 31, 1984

[87] PCT Pub. No.: WO84/04542

PCT Pub. Date: Nov. 22, 1984

[30] Foreign Application Priority Data

May 9, 1983 [SE] Sweden ............................. 8302654

[51] Int. Cl.$^4$ ............................................... C12P 7/08
[52] U.S. Cl. .................... 435/163; 435/161; 435/938; 435/921; 435/801
[58] Field of Search ............... 435/161, 163, 165, 164

[56] References Cited

U.S. PATENT DOCUMENTS 4,359,534 11/1982 Kurtzman et al. ................. 435/161
4,368,268 1/1983 Gong ................................. 435/161
4,477,569 10/1984 Schneider et al. ................. 435/161
4,511,656 4/1985 Gong ................................. 435/161

OTHER PUBLICATIONS

Du Preg, "Fermentation of Dxylose to Ethanol by A Strain of Candida Shehatae", Chemical Abstracts, vol. 99, Abstract No. 20889u, (1983).

Inst. Ferm. Research, "Ethanol Production from Xylose", Chemical Abstracts, vol. 100, Abstract No. 4808a, (1984).

Bruinenberg et al., "NADH Linked Aldose Reduclose the Key to Anaerobic Alcohol Fermentation of Xylose by Yeasts", Chem Abst 101: 128823s.

Toivola et al., Alcoholic Fermentation of D-Xylose by Yeasts, Chemical Abstracts, vol. 101, Abstract No. 70990a, (1984).

Maleszka et al., "Yeasts that Ferment D-Cellobiose As Well As D-Xylose", Biotechology Letters, vol. 4, pp. 133–136 (1982).

*Primary Examiner*—R. B. Penland
*Attorney, Agent, or Firm*—Davis Hoxie Faithfull & Hapgood

[57] ABSTRACT

A method for fermenting xylose-containing substance, such as a lignocellulosic degradation product into ethanol. Yeast of the species *Pichia stipitis* and/or *Pichia segobiensis* and/or *Candida shehatae* are utilized for the fermentation.

8 Claims, No Drawings

METHOD FOR PRODUCING ETHANOL FROM XYLOSE-CONTAINING SUBSTANCE

This invention relates to a method for producing ethanol from a xylose-containing substance, comprising fermenting said substance with a yeast. Such methods have been disclosed recently in the U.S. Pat. Nos. 4,359,534 and 4,368,268, wherein the fermentation utilizes the yeast *Pachysolen tannophilus* and yeast mutants from the strain Candida sp. The obejct of the present invention is to provide a method for fermenting xylose in a high yield.

The yeasts for use in the invention are *Pichia stipitis*, *Pichia segobiensis* and *Candida shehatae*. The *P. stipitis* type strain CBS 5773 (NRRL Y-7124, T) was originally isolated from an insect larvae and was designated by Pignal. The standard description of *P. stipitis*, made by Kreger-van Rij, 1970 (The Yeasts-A Taxonomic Study (Lodder, J. ed.) pp. 533–535, North-Holland Publishing Company-Amsterdam, London) is as follows:

Growth in malt extract: After 3 days at 25° C. the cells are spherical to oval (2–7.5)×2.5–7.5) μm; single or in pairs. A sediment is formed. After one month at 17° C. a sediment and, occasionally, a ring are present.

Growth on malt agar: After 3 days at 25° C. the cells are spherical to short-oval, (2.5–4.5)×(2.5–6) μm; single or in pairs. Pseudomycelial cells may occur up to 15 μm long. After one month at 17° C. the streak culture is cream-colored, occasionally with a reddish tinge, soft, smooth or delicately wrinkled in the middle, and semi-glossy. The edge is fringed with pseudomycelium.

Slide cultures on potato- and corn meal agar: Pseudomycelium is abundantly formed. It is more or less branched and consists of long pseudomycelial cells with small blastospores.

Formation of ascospores: Conjugation between mother cell and bud or between two single cells precedes ascus formation. The cells may form protuberances of various lengths. The spores are hat-shaped; two are formed per ascus. They are easily liberated from the ascus. Spores were observed in the three strains studied on YM-, Difco malt extract- and corn meal agar.

Fermentation:

| | |
|---|---|
| Glucose + (slow) | Trehalose + (very weak) or − |
| Galactose + (slow) | Lactose − |
| Sucrose − | Raffinose − |
| Maltose + (slow) | |

Assimilation of carbon compounds:

| | |
|---|---|
| Glucose + | D-Ribose + |
| Galactose + | L-Rhamnose + |
| L-Sorbose − | Ethanol + |
| Sucrose + | Glycerol + |
| Maltose + | Erythritol + |
| Cellobiose + | Ribitol + |
| Trehalose + | Galactitol − |
| Lactose + | D-Mannitol + |
| Melibiose − | D-Glucitol + |
| Raffinose − | α-Methyl-D-glucoside + |
| Melezitose + | Salicin + |
| Inulin − | DL-Lactic acid + |
| Soluble starch + | Succinic acid + |
| D-Xylose + | Citric acid + |
| L-Arabinose + | Inositol − |
| D-Arabinose − | |

Splitting of arbutin: Positive
Assimilation of potassium nitrate: Negative
Growth in vitamin-free medium: Negative or very weakly positive.
Growth on 50% (w/w) glucose-yeast extract agar: Negative
Growth at 37° C.: Positive.

In addition to the above-mentioned fermentable substrates it has unexpectedly been found that *P. stipitis* also ferments D-xylose. *P. segobiensis* is described in the following reference: J. Santa Maria and G. G. Aser, An. Inst. Nac. Invest. Agrarias, Ser. General 5 (1977) 45–50. It has been found that this yeast ferments D-xylose to ethanol to a degree comparable to that of *P. stipitis*. All *P. stipitis* strains tested—CBS 5773, CBS 5774, CBS 5775, CBS 5776, CBS 6054, and *P. segobiensis* strain CBS 6857—share this characteristic. All these strains are therefore contemplated for use in the disclosed process. Also the tentatively (Lodder: The Yeasts (1970) p. 535, 1046, 1047) imperfect form of *P. stipitis* (*Candida shehatae*) ferments D-xylose to ethanol and is therefore also contemplated for use in the disclosed process.

All D-xylose-containing substrates are suitable in the disclosed process provided they do not contain any constituents which are severely inhibitory to the process.

Since available glucose also will be fermented to ethanol, hydrolyzed cellulose and hydrolyzed hemicellulose or mixtures thereof are particularly suited as substrates in the disclosed process. Hence, as raw material for the process could serve any lignocellulose material containing cellulose and hemicellulose such as wood, grass, straw, bagasse etc. Also suited as substrates are waste fluids, such as spent sulphite liquor, containing D-xylose, besides other sugars if any. It is understood that the predominant monosaccharide found in hydrolyzed hemicellulose is D-xylose.

The disclosed process involves the fermentation in an aqueous medium of D-xylose, and D-glucose if present, to ethanol. The chemical and physical conditions of the medium must otherwise be as to maintain cell viability, as known by a person skilled in the art.

When cell growth is required, the ethanol concentration should not exceed 45 g/l. At 30 g/l, the growth rate is considerably retarded. Ethanol yield is reduced at ethanol concentrations at or above 30 g/l.

*P. stipitis* grows well at 28°–32° C. Fermentation is supported in the temperature range 15°–40° C. The highest rate is observed between 30° C. and 37° C., with 32°–34° C. being optimum for the ethanol production rate.

Growth of *P. stipitis* CBS 5773 occurs in the pH interval 3–7. pH 5 results in a slightly better growth than do pH 4 and pH 6. Ethanol production rate is good between pH 3 and pH 8, with pH 6 being about maximum. Since it is desirable to perform fermentation at the lowest possible pH in order to minimize the risk of infection, it should be observed, that at pH 4 the production rate is more than 90% of maximum and the growth rate is also satisfactory at this pH.

Ethanol production proceeds in an anaerobic medium. The ethanol yield of anaerobic fermentation is approximately equal to that of a fermentation at a limited air supply, although the fermentation rate is somewhat lower.

In a typical batch-type fermentation a cell suspension of *P. stipitis* obtained from a preculture preferably in exponential growth phase, is supplied with D-xylose. The conditions are adjusted and maintained within the range defined above. Ethanol production is thereby initiated and will be continued at the rate governed by the actual cell concentration and conditions otherwise prevailing. Provided the conditions are maintained within the range defined above and the cells are kept viable, ethanol production will not discontinue until the D-xylose is depleted.

In U.S. Pat. No. 4,359,534 a process is described where the yeast *Pachysolen tannophilus* is used to ferment a D-xylose-containing substance. It is reported that aeration is a prerequisite for enhanced ethanol production. The highest yield reported in this patent is 0.34 g ethanol/g D-xylose. In U.S. Pat. No. 4,368,268 a similar process is described where a mutant strain of Candida sp., XF 217 is used to ferment D-xylose to ethanol. It is reported that oxygen must be available for enhanced ethanol production from D-xylose. The highest yield reported in this patent is that demonstrated in FIGS. 1 and 2 showing aerobic fermentation from which a yield of 0.42 g ethanol/g D-xylose may be estimated.

A small amount of air (oxygen) is necessary for cell growth. The ethanol yield in aerobic fermentation using *P. stipitis* with a limited amount of air is about the same as in anaerobic fermentation. This makes possible a fermentation process where conditions favourable for growth and efficient fermentation can be met simultaneously. The effect of a small amount of oxygen is thus twofold; it makes the necessary cell growth possible and it increases the specific ethanol productivity of the cells.

The highest yield obtained in a single fermentation experiment is 0.46 g ethanol/g D-xylose. It is our conviction that 3/2 molecules of ethanol are formed for each molecule of D-xylose.

This corresponds to a maximum theoretical yield of 0.46 g ethanol/g D-xylose consumed. Hence, the yield above is 100%. Usually, the yield is slightly lower, 0,43-0,45 g/g (=93-98% of maximum).

EXAMPLES

The following examples are offered in order to more fully describe the presently disclosed process, but are not to be construed as limiting the scope of the invention defined by the claims.

General Experimental Procedure

Agar slant cultures of *Pichia stipitis*, strains CBS 5773, 5774, 5775, 5776, 6054, *Pichia segobiensis* CBS 6857 and *Candida shehatae*, strains CBS 5712 and 5813 were obtained from Laboratorium voor Microbiologie, Technische Hogeschool Delft, Delft. The cultures were maintained on agar slants at 30° C. The slant medium contained 20 g/l D-xylose, 7 g/l yeast extract and 15 g/l agar. Unless stated otherwise, the liquid media for yeast propagation contained 7 g/l yeast extract, 10 g/l D-xylose and a mineral base of $(NH_4)_2SO_4$ (2.35 g/l), $KH_2PO_4$ (0.55 g/l), $MgSO_4 \times 7H_2O$ (0.25 g/l), $Na_2HPO_4 \times 12H_2O$ (0.25 g/l), $CaCl_2 \times 2H_2O$ (20 mg/l), and trace elements ($H_3BO_3$ (0,5 mg/l), $MnSO_4 \times 4H_2O$ (0.2 mg/l), $ZnSO_4 \times 7H_2O$ (0.2 mg/l), $CuSO_4 \times 5H_2O$ (0.23 mg/l), $FeSO_4 \times 7H_2O$ (1.25 mg/l), $(NH_4)_6Mo_7O_{24} \times 4H_2O$ (0.1 mg/l), $H_2SO_4$ (0.5 mg/l), $Co(NO_3)_2 \times 6H_2O$ (0.25 mg/l), KJ(0.05 mg/l)) (pH 5.0). In cases where a different xylose concentration was used, the relative proportions of other medium components were the same as above. Incubation was made on a rotary shaker at 30° C., unless otherwise stated.

Unless aerobic conditions are stated, fermentation refers to the condition where the gas phase in the test vessel consisted of $CO_2$ and pressure equilibration was allowed for by means of a syringe through the rubber stopper sealing the vessel. The general experimental procedure implied aerobic propagation of yeast cells in a liquid medium as described above, harvesting the cells in exponential growth phase, by centrifugation, and resuspending them in fresh medium resulting in a final fermentation mixture containing (approx.) 5 g (dry weight) cells/l. Produced ethanol was measured by gas chromatography or high pressure liquid chromatography (HPLC). D-xylose and xylitol were quantified by HPLC. Cell growth (expressed as g/l, D.W.) was measured as optical density at 620 nm and the corresponding cell concentration was calculated by multiplication with an experimentally determined factor.

EXAMPLE 1

Yield measurements

The experiment was performed according to the General Experimental Procedure, however, the xylose concentration used was 20 g/l. The xylose was completely fermented by all strains tested. Ethanol yield and specific fermentation rate are shown in table 1:

TABLE 1

| Strain | Ethanol yield g ethanol/ g xylose | Specific fermentation rate g ethanol/g cells. h |
|---|---|---|
| *P. stipitis* CBS 5773 | 0.44 | >0.10 |
| *P. stipitis* CBS 5774 | 0.46 | >0.10 |
| *P. stipitis* CBS 5775 | 0.45 | >0.10 |
| *P. stipitis* CBS 5776 | 0.45 | >0.10 |
| *P. stipitis* CBS 6054 | 0.43 | >0.10 |
| *P. segobiensis* CBS 6857 | 0.45 | >0.10 |
| *C. shehatae* CBS 5712 | 0.45 | 0.08 |
| *C. shehatae* CBS 5813 | 0.44 | >0.10 |

EXAMPLE 2

Effect of oxygen

In an experiment, typical for *P. stipitis*, to a medium containing 15 g/l xylose and other constituents as described above was added 2,3 g/l (dry weight) cells of *P. stipitis* strain CBS 5776. Fermentation was performed in two gently agitated vessels, one of which was initially gassed with high purity carbon dioxide, and the other vessel was initially gassed with air. The gas:liquid ratio was about 5:1. The vessels were sealed with rubber gaskets and pressure equilibration was made possible through syringes. Samples were withdrawn during the fermentation for determination of ethanol, xylose, xylitol and cell density. The results are shown in table 2:

TABLE 2

| Initial gas phase | Ethanol yield g ethanol/ g xylose | Specific fermentation rate g ethanol/ g cells, hour | Xylitol g xylitol/ g xylose | Cell growth g cells/g xylose | Residual xylose g/l |
|---|---|---|---|---|---|
| $CO_2$ | 0.43 | 0.16 | 0.03 | 0 | 0 |

TABLE 2-continued

| Initial gas phase | Ethanol yield g ethanol/ g xylose | Specific fermentation rate g ethanol/ g cells, hour | Xylitol g xylitol/ g xylose | Cell growth g cells/g xylose | Residual xylose g/l |
| --- | --- | --- | --- | --- | --- |
| air | 0.44 | 0.23 | 0 | 0.15 | 0 |

The ethanol yield is close to the theoretical yield (0.46 g/g) and not significantly reduced at anaerobic conditions. However a limited access to air (oxygen) during fermentation stimulates the specific fermentation rate, reduces xylitol production to zero, and supports cell growth.

EXAMPLE 3

Effect of pH on fermentation rate

The experiment was performed according to the General Experiment Procedure, however, prior to inoculation pH in eight different fermentation media was adjusted to different values. The initial fermentation rate was estimated by determining the amount of ethanol produced between the 30th and 60th minute. pH was measured after 60 minutes. Table 3 shows the results.

TABLE 3

| P. stipitis strain | % of maximum initial fermentation rate | | | | | | | |
| --- | --- | --- | --- | --- | --- | --- | --- | --- |
| Initial pH | 2.0 | 3.0 | 4.0 | 5.0 | 6.0 | 7.0 | 8.0 | 9.0 |
| Final pH | 2.3 | 3.0 | 4.1 | 4.8 | 5.8 | 6.5 | 6.9 | 8.5 |
| CBS 5773 | 36 | 74 | 94 | 97 | 100 | 100 | 90 | 0 |
| CBS 5774 | 25 | 81 | 96 | 88 | 79 | 100 | 58 | 0 |
| CBS 5775 | 5 | 5 | 81 | 73 | 90 | 100 | 68 | 0 |
| CBS 5776 | 48 | 81 | 100 | 85 | 96 | 85 | 96 | 0 |
| CBS 6054 | 37 | 70 | 89 | 91 | 100 | 91 | 83 | 0 |

EXAMPLE 4

Effect of temperature on growth rate

The influence of temperature on growth rate was studied for five *P. stipitis* strains. Shake flash with medium as described in the General Experimental Procedure were inoculated with 0.05 g/l of cells, covered with cotton filters for free air access and incubated in a rotary shaker at 8 different temperatures. The results are shown in table 4:

TABLE 4

| P. stipitis strain | Specific growth rate μ[h⁻¹] | | | | | | | | |
| --- | --- | --- | --- | --- | --- | --- | --- | --- | --- |
| | temperature, °C. | | | | | | | | |
| | 20 | 25 | 28 | 30 | 32 | 34 | 36 | 38 | 40 |
| CBS 5773 | 0.26 | 0.37 | 0.39 | 0.46 | 0.41 | 0.39 | 0.17 | 0 | 0 |
| CBS 5774 | 0.24 | 0.32 | 0.37 | 0.50 | 0.46 | 0.41 | 0.28 | 0.12 | 0 |
| CBS 5775 | 0.23 | 0.33 | 0.43 | 0.35 | 0.31 | 0.29 | 0 | 0 | 0 |
| CBS 5776 | 0.22 | 0.37 | 0.41 | 0.53 | 0.46 | 0.37 | 0.28 | 0.06 | 0 |
| CBS 6054 | 0.18 | 0.39 | 0.43 | 0.46 | 0.50 | 0.39 | 0.35 | 0.13 | 0 |

EXAMPLE 5

Effect of temperature on fermentation rate.

The experiment was performed according to example 3, however, pH was 5.0 and the fermentation was performed at different temperatures. Table 5 shows the results:

TABLE 5

| P. stipitis strain | % of maximum initial fermentation rate | | | | | | | | |
| --- | --- | --- | --- | --- | --- | --- | --- | --- | --- |
| | temperature, °C. | | | | | | | | |
| | 15 | 20 | 25 | 28 | 30 | 32 | 34 | 37 | 40 |
| CBS 5773 | 5 | 11 | 38 | 62 | 87 | 94 | 100 | 80 | 45 |
| CBS 5774 | | 23 | 48 | 67 | 85 | 100 | 94 | 86 | 72 |
| CBS 5775 | | 8 | 35 | 52 | 75 | 88 | 100 | 90 | 66 |
| CBS 5776 | | 7 | 40 | 68 | 84 | 97 | 100 | 95 | 53 |
| CBS 6054 | | 22 | 33 | 58 | 82 | 100 | 91 | 87 | 63 |

EXAMPLE 6

Effect of ethanol on growth

The experiment was performed according to example 4, however, ethanol was added at three different concentrations and the incubation temperature was 30° C. Table 6 shows the results:

TABLE 6

| | Cell growth in g/l | | |
| --- | --- | --- | --- |
| | Ethanol, g/l | | |
| Strain | 0 | 30 | 45 |
| P. stipitis CBS 5773 | 2.1 | 0.7 | 0 |
| P. stipitis CBS 5774 | 2.6 | 1.2 | 0.3 |
| P. stipitis CBS 5775 | 1.3 | 0 | 0 |
| P. stipitis CBS 5776 | 2.2 | 1.0 | 0 |
| P. stipitis CBS 6054 | 2.4 | 1.1 | 0 |
| P. segobiensis CBS 6857 | 2.2 | 0.1 | 0 |
| C. shehatae CBS 5712 | 0.7 | 0 | 0 |
| C. shehatae CBS 5813 | 1.0 | 0 | 0 |

EXAMPLE 7

Effect of ethanol on ethanol yield

The experiment was performed according to the General Fermentation Procedure, however, ethanol was added at four different concentrations. Incubation temperature was 30° C. for all *P. stipitis* strains and 25° C. for *P. segobiensis* CBS 6857. Table 7 shows the results:

TABLE 7

| | % of maximum yield (g ethanol/g xylose) | | | |
| --- | --- | --- | --- | --- |
| | Ethanol, g/l | | | |
| Strain | 0 | 30 | 45 | 60 |
| P. stipitis CBS 5773 | 100 | 80 | 51 | 26 |
| P. stipitis CBS 5774 | 100 | 80 | 51 | 8 |
| P. stipitis CBS 5775 | 100 | 61 | 76 | 45 |
| P. stipitis CBS 5776 | 100 | 90 | 76 | 34 |
| P. stipitis CBS 6054 | 100 | 100 | 68 | 29 |
| P. segobiensis CBS 6857 | 100 | 66 | 80 | 55 |

EXAMPLE 8

Spent sulphite liquor was neutralized to pH with KOH, supplied with yeast extract and mineral nutrients as described in General Experimental Procedure and inoculated with 5 g/l *P. stipitis* CBS 6054.

Fermentation was performed in a cotton-stoppered shake flask at 30° C. during 24 hours. The result is shown in table 8:

TABLE 8

| Fermentation time hours | Concentration g/l | | | | |
|---|---|---|---|---|---|
| | Glucose | Mannose | Galactose | Xylose | Ethanol |
| 0 | 4.6 | 11.0 | 2.5 | 6.2 | 0 |
| 24 | 0 | 0 | 0 | 0.4 | 9.9 |

It is understood that the experimental conditions in this example are not optimized for ethanol yield.

We claim:

1. A method for producing ethanol from a D-xylose containing substance, comprising fermenting said substance with a yeast of the genus Pichia or its imperfect forms belonging to the genus Candida, selected from the species consisting of *Pichia stipitis, Pichia segobiensis* and *Candida shehatae,* under aerobic or anaerobic conditions to produce ethanol in a yield, in the absence of constituents severely inhibitory to the process, of at least 0.43 g. ethanol, per g. of D-xylose.

2. A method according to claim 1, wherein the yeast is *Pichia stipitis,* a strain is selected from the group consisting of CBS 5773, CBS 5774, CBS 5775, CBS 5776, CBS 6054.

3. A method according to claim 1, wherein the yeast *Pichia segobiensis* is the strain CBS 6857.

4. A method according to claim 1, wherein the yeast is *Candida shehatae,* a strain is selected from the group consisting of CBS 5813, CBS 5712.

5. A method according to claim 2, wherein the pH is maintained within the range of about 2 to 8, and the temperature within the range of about 15° C. to 40° C.

6. A method according to claim 5, wherein the pH is maintained at 4–7 and the temperature at 30°–37° C.

7. A method according to claim 1, wherein the oxygen concentration in the fermenting medium is maintained so as to imply essentially anaerobic conditions.

8. A method according to claim 1, wherein said D-xylose-containing substance is a lignocellulosic degradation product.

* * * * *